US 9,776,246 B2

(12) United States Patent
Lawrynowicz et al.

(10) Patent No.: US 9,776,246 B2
(45) Date of Patent: Oct. 3, 2017

(54) METHOD FOR FABRICATING A BIOCOMPATIBLE MATERIAL HAVING A HIGH CARBIDE PHASE AND SUCH MATERIAL

(71) Applicant: Howmedica Osteonics Corp., Mahwah, NJ (US)

(72) Inventors: Daniel E. Lawrynowicz, Monroe, NY (US); Aiguo Wang, Wayne, NJ (US); Zongtao Zhang, Riverdale, NJ (US); Haitong Zeng, Oakland, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 277 days.

(21) Appl. No.: 14/553,343

(22) Filed: Nov. 25, 2014

(65) Prior Publication Data

US 2015/0068362 A1 Mar. 12, 2015

Related U.S. Application Data

(63) Continuation of application No. 11/728,678, filed on Mar. 26, 2007, now Pat. No. 8,920,534.

(51) Int. Cl.
*B22F 3/115* (2006.01)
*B22F 3/08* (2006.01)
(Continued)

(52) U.S. Cl.
CPC .......... *B22F 9/082* (2013.01); *A61L 27/427* (2013.01); *B22D 23/00* (2013.01); *B22F 1/0007* (2013.01);
(Continued)

(58) Field of Classification Search
None
See application file for complete search history.

(56) References Cited

U.S. PATENT DOCUMENTS 2,685,543 A   8/1954   Sindeband
4,153,453 A   5/1979   Hart et al.
(Continued)

FOREIGN PATENT DOCUMENTS

JP   60-003299 A   1/1985

OTHER PUBLICATIONS

Gordon England, Plasma Spray—Thermal Spray Coating Process, www.gordonengland.co.uk/ps.htm (2001), Last visited May 24, 2010.
(Continued)

*Primary Examiner* — Yoshitoshi Takeuchi
(74) *Attorney, Agent, or Firm* — Lerner, David, Littenberg, Krumholz & Mentlik, LLP

(57) ABSTRACT

A method of fabricating a material having a high concentration of a carbide constituent. The method may comprise adding a carbide source to a biocompatible material in which a weight of the carbide source is at least approximately 10% of the total weight, heating the carbide source and the biocompatible material to a predetermined temperature to melt the biocompatible material and allow the carbide source to go into solution to form a molten homogeneous solution, and impinging the molten homogeneous solution with a high pressure fluid to form spray atomized powder having carbide particles. The size of a particle of carbide in the atomized powder may be approximately 900 nanometers or less. The biocompatible material may be cobalt chrome, the carbide source may be graphite, and the fluid may be a gas or a liquid.

9 Claims, 3 Drawing Sheets

(51) Int. Cl.
- *C23C 4/00* (2016.01)
- *C23C 4/04* (2006.01)
- *C23C 4/06* (2016.01)
- *C23C 4/067* (2016.01)
- *C23C 4/10* (2016.01)
- *C23C 4/12* (2016.01)
- *C23C 4/123* (2016.01)
- *C23C 4/126* (2016.01)
- *C23C 4/129* (2016.01)
- *C23C 4/131* (2016.01)
- *C23C 4/134* (2016.01)
- *C23C 4/137* (2016.01)
- *B22F 9/08* (2006.01)
- *A61L 27/42* (2006.01)
- *B22D 23/00* (2006.01)
- *B22F 1/00* (2006.01)
- *C22C 32/00* (2006.01)
- *A61F 2/02* (2006.01)

(52) U.S. Cl.
CPC ........... *C22C 32/0052* (2013.01); *A61F 2/02* (2013.01); *B22F 2009/0848* (2013.01); *B22F 2302/10* (2013.01)

(56) References Cited

U.S. PATENT DOCUMENTS

| | | | |
|---|---|---|---|
| 4,687,487 A | 8/1987 | Hintermann | |
| 5,242,479 A | 9/1993 | Movchan et al. | |
| 5,256,243 A | 10/1993 | Kida | |
| 5,370,694 A | 12/1994 | Davidson | |
| 5,480,438 A | 1/1996 | Arima et al. | |
| 5,509,933 A | 4/1996 | Davidson et al. | |
| 5,713,947 A | 2/1998 | Davidson | |
| 5,868,796 A | 2/1999 | Buechel et al. | |
| 5,954,724 A | 9/1999 | Davidson | |
| 6,139,585 A | 10/2000 | Li | |
| 6,187,045 B1 | 2/2001 | Fehring et al. | |
| 6,312,473 B1 | 11/2001 | Oshida | |
| 6,425,922 B1 | 7/2002 | Pope et al. | |
| 6,447,550 B1 | 9/2002 | Hunter et al. | |
| 6,585,772 B2 | 7/2003 | Hunter et al. | |
| 6,652,588 B2 | 11/2003 | Hayes, Jr. et al. | |
| 6,723,177 B2 | 4/2004 | Dearnaley et al. | |
| 6,773,520 B1 | 8/2004 | Fehring et al. | |
| 6,881,229 B2 | 4/2005 | Khandkar et al. | |
| 7,771,775 B2 | 8/2010 | Lawrynowicz et al. | |
| 2001/0004473 A1 | 6/2001 | Strutt et al. | |
| 2002/0038149 A1 | 3/2002 | Hall et al. | |
| 2002/0052659 A1 | 5/2002 | Hayes et al. | |
| 2003/0049485 A1 | 3/2003 | Brupbacher et al. | |
| 2003/0125808 A1 | 7/2003 | Hunter et al. | |
| 2003/0171820 A1 | 9/2003 | Wilshaw et al. | |
| 2003/0220696 A1 | 11/2003 | Levine et al. | |
| 2004/0002766 A1 | 1/2004 | Hunter et al. | |
| 2004/0043230 A1 | 3/2004 | Hatono et al. | |
| 2004/0133283 A1 | 7/2004 | Shetty | |
| 2004/0243241 A1 | 12/2004 | Istephanous et al. | |
| 2004/0249469 A1 | 12/2004 | Cohen et al. | |
| 2005/0025896 A1 | 2/2005 | Grinberg et al. | |
| 2005/0026001 A1 | 2/2005 | Taylor | |
| 2005/0107870 A1 | 5/2005 | Wang et al. | |
| 2005/0112411 A1 | 5/2005 | Gray et al. | |
| 2005/0241736 A1 | 11/2005 | Bell et al. | |
| 2006/0184251 A1 | 8/2006 | Zhang et al. | |
| 2007/0243335 A1* | 10/2007 | Belashchenko | B22F 1/0096 427/451 |
| 2008/0241570 A1 | 10/2008 | Lawrynowicz et al. | |
| 2009/0324442 A1 | 12/2009 | Lawrynowicz et al. | |

OTHER PUBLICATIONS

Parasiris et al., Consolidation of advanced WC-Co powders, International Journal of Refractory Metals & Hard Metals, 2000 vol. 18 pp. 23-31.

Klaus Dreyer and Henk van den Berg, Carbide makers rise to teh challenge, Metal Powder Report, vol. 54, Issue 4, Apr. 1999, pp. 14-19.

Lovelock, Powder/Processing/Structure Relationships in WC-Co Thermal Spray Coatings, 7 J. Thermal Spray Tech. 357-373 (1998).

* cited by examiner

METHOD FOR FABRICATING A BIOCOMPATIBLE MATERIAL HAVING A HIGH CARBIDE PHASE AND SUCH MATERIAL

CROSS-REFERENCE TO RELATED APPLICATION

This application is a continuation of U.S. application Ser. No. 11/728,678, filed on Mar. 26, 2007, the disclosure of which is incorporated herein by reference.

BACKGROUND OF THE INVENTION

The present invention relates to a method of fabricating a biocompatible material having a relatively high concentration of a carbide or carbon constituent which may be used in the fabrication of medical components, and to such material.

Medical components, such as medical implant components, may be formed or fabricated from a material or materials having good wear properties. As an example, such components may be formed or fabricated from a biocompatible material such as cobalt chrome or a cobalt chrome alloy having a carbide content. For medical implant components, such carbide content may comprise a relatively small percentage of the final material, such as typically only approximately 3-5% by weight thereof. Although the percentage of the carbide content of some biocompatible materials other than cobalt chrome or a cobalt chrome alloy for use in non-medical implant type components may be higher, the size of the particles of carbide therein may be relatively large. As hereinafter more fully described, such relatively large size carbide particles may have undesirable effects.

The carbide content is primarily responsible for the good wear properties of the above-mentioned cobalt chrome alloy. As is to be appreciated, if the percentage of carbide content in a material (such a cobalt chrome alloy) could be increased, then the wear properties of the resultant alloy or material could be improved. However, increasing the carbide content may result in a decrease of other properties. For example, increasing the carbide content in a biocompatible material (such as cobalt chrome) may reduce the fatigue life, strength, corrosion resistance, and toughness, may produce a material which is relatively highly brittle, and/or may reduce the uniformity of the material and produce a material which is relatively highly non-uniform.

The decrease in the above-identified properties (especially the uniformity) may make the resultant material difficult to machine. More specifically, if the carbide content is increased beyond a certain amount, the carbide content in the biocompatible material may not completely mix with the biocompatible material. As a result, the biocompatible material may have some of the carbide constituent or particles completely mixed therein and may have some of the carbide particles which are not completely mixed or not at all mixed therein. Such situation may be considered similar to that of adding sugar to a glass of water. In this later situation, after a certain amount of sugar is added, the sugar no longer mixes or dissolves in the water. Instead, some of the sugar remains in a non-dissolved or a not completely dissolved state.

To further describe the above-mentioned machining difficulty of a material having an increased carbide content, consider the parts illustrated in FIGS. 3A and 3B. With reference to FIG. 3A, unmixed carbide particles 90 contained within an item 92 formed from biocompatible material and carbide may be relatively large, such as between 5-20 microns in size or length. Additionally, the carbide particles 90 may be relatively strong. As a result, machining or cutting such material may be difficult if not impossible. For example, and with reference to FIG. 3B, if a surface 94 of the item 92 to be machined contains a number of relatively large carbide particles 90, then during a machining operation thereof when a cutting tool 96 encounters a portion 98 of a respective carbide particle 90, instead of just the desired portion of such carbide particle being cut, the entire particle may be removed thereby leaving a depression in the surface. As such, it may be very difficult, if not impossible, to properly machine surface 94 (having the relatively large size carbide particles 90) to a desired thickness or dimension T. In other words, even if the item 92 is actually machined so as to have thickness/dimension T, the machined surface may contain a number of depressions or voids and, as such, may not have a desired surface roughness or finish. Additionally, since the carbide particles 90 are relatively strong, the cutting tool 96 may be damaged during the machining or cutting operation.

Thus, merely increasing the carbide content such as in an as-cast cobalt chrome molygdmum (CoCrMo alloy) may result in a decrease in several properties (such as fatigue life, strength, corrosion resistance, and toughness)) and may produce a material having relatively large sized carbide particles which may cause a machining operation to be difficult.

In any event, and possibly for the reasons described above, a biocompatible material such as cobalt chrome or a cobalt chrome alloy having a relatively high carbide content has not been provided to date which may be used in the fabrication of medical components.

It would be advantageous to provide a technique for producing a biocompatible material or alloy, which may be used in the fabrication of medical implant components, having a carbide content of approximately 10% or higher by weight, in which the size of a carbide particle is approximately 900 nanometers or less so as to increase the wear properties of the medical implant components as compared to that of conventional medical implant components and to enable relatively easy machining thereof. It would be further advantageous to provide such technique whereby the resultant biocompatible material or alloy would have relatively good fatigue properties, would not be highly brittle, and would be relatively uniform or homogeneous.

SUMMARY OF THE INVENTION

In accordance with an aspect of the present invention, a method of fabricating a material having a high concentration of a carbide constituent is provided. Such method may comprise adding a carbide source to a biocompatible material in which a weight of the carbide source is at least approximately 10% of the total weight, heating the carbide source and the biocompatible material to a predetermined temperature to melt the biocompatible material and allow the carbide source to go into solution so as to form a molten homogeneous solution, and impinging the molten homogeneous solution with a high pressure fluid so as to form spray atomized powder having carbide particles, in which the size of a particle of carbide in the atomized powder is approximately 900 nanometers or less.

The fluid may be a gas (such as argon or nitrogen) or a liquid (such as water). The size of the carbide particle in the atomized powder may be within a range of approximately 10-200 nanometers. The predetermined temperature may be approximately 200-300 degrees Centigrade over a melting temperature of the biocompatible material. The biocompatible material may be cobalt chrome and the carbide source may be graphite.

In accordance with another aspect of the present invention, a method of fabricating a material having a high concentration of a carbide constituent is provided. Such method may comprise providing a carbide source in a powder form and a biocompatible material in a powder form, and mixing the carbide source and the biocompatible material to form a powder mixture thereof, wherein a weight of the carbide source is approximately 10% or more of the total weight and wherein a particle of the carbide source in the powder form has a size of approximately 900 nanometers or less. The biocompatible material may be cobalt chrome and the carbide source may be graphite.

In accordance with yet another aspect of the present invention, a material for use in fabricating a medical implant component is provided. Such material may be formed from a carbide source and a biocompatible material, in which a weight of the carbide source is at least approximately 10% of a total weight of the carbide source and the biocompatible material and in which a particle of the carbide source has a size of approximately 900 nanometers or less.

DETAILED DESCRIPTION

The present invention may be used to fabricate or form a biocompatible material or alloy having a relatively high concentration of a carbon or carbide constituent. As hereinafter more fully described, the carbide concentration or the amount of carbide may be approximately ten (10) percent or higher of the total weight of the formed biocompatible material. In fact, such carbon or carbide content may have any value from ten (10) percent up to nearly 100 percent, such as 15, 25, 50, 75 or even approximately 99 percent of the total weight of the formed biocompatible material. Such formed biocompatible material may be used in the fabrication of medical implant components. For example, such material may be utilized to coat one or more surfaces of a medical implant component, such as an acetabular cup, a femoral head, a femoral knee, a tibial knee, a shoulder component, or a spine component by use of a spraying operation.

A system 10 which may be utilized to fabricate or form a biocompatible material or alloy having a relatively high concentration of a carbon or carbide constituent in accordance with an embodiment of the present invention will now be described with reference to FIGS. 1, 2A, and 2B. In general, the system 10 may be utilized to combine a biocompatible material or alloy with a carbon or carbide source so as to obtain the desired material. The biocompatible material or alloy may be one of cobalt chrome, titanium (Ti), a titanium alloy, zirconium (Zr), a zirconium alloy, stainless steel, a cobalt based super alloy, and so forth; and the carbon or carbide source may be one of graphite, coke, pitch, diamond, diamond dust and so forth.

Figure 1:
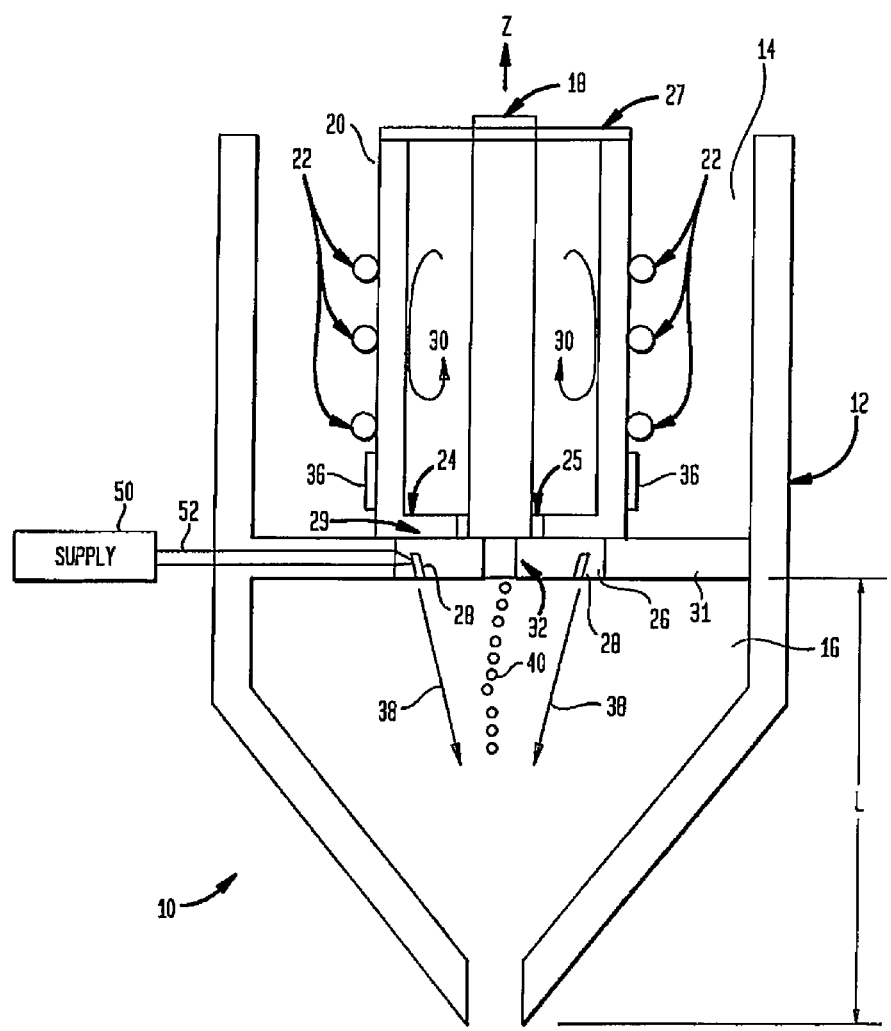
FIG. 1 is a cross-sectional diagram of a system to which reference will be made in explaining a method for producing a material having a relatively high carbide content in accordance with an embodiment of the present invention.

FIG. 1 illustrates a cross-sectional diagram of system or apparatus 10. As shown therein, system or apparatus 10 may generally include a vessel or container 12, a container or crucible 20, a stopper rod 18, and an atomizer 26.

The vessel 12 may have a first portion 14 and a second portion 16. The vessel 12 may be fabricated from a metal or other type material. The vessel may be configured such that the first portion 14 is large enough to hold the crucible 20 and such that the second portion 16 is sufficiently large to enable an atomization process to be properly performed, as herein below more fully described. With regard to the second portion 16, the length L thereof may have a value in the range of approximately 2 feet to 10 feet.

The crucible 20 may be fabricated from a ceramic or other non-metal material and may have a generally cylindrical shape. The crucible 20 may have a base portion 24 located at the bottom thereof. A hole 25 may be located in the center of the base portion 24 and may be sized or configured so as to allow the rod 18 to pass therethrough and sit on the atomizer 26. The crucible 20 may be adapted to receive a number of materials which are to be combined. Such materials may include a biocompatible material or alloy (such as cobalt chrome) and a carbon or carbide source (such as graphite). A top portion 27 may be placed on top of the crucible 20 so that during operation the crucible may be substantially closed.

Figure 2A:
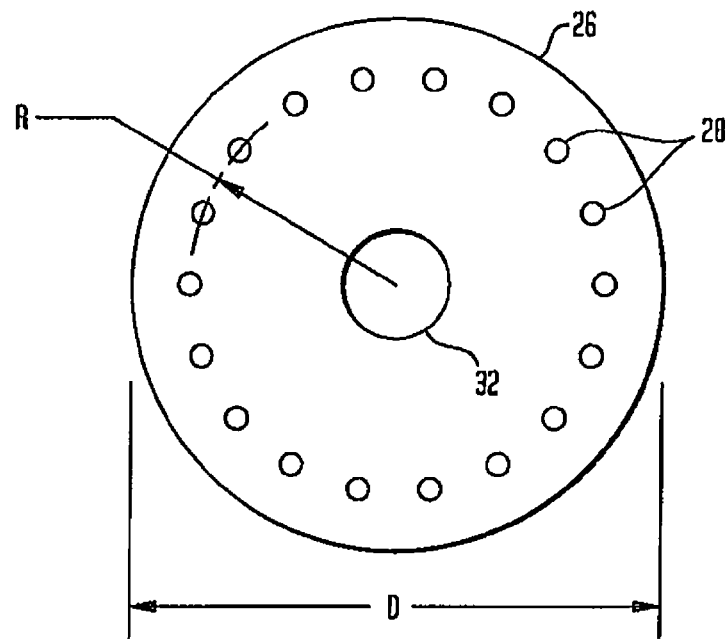
FIGS. 2A and 2B are diagrams of a top view and a side view, respectively, of a base plate which may be used in the system of FIG. 1.
Figure 2B:
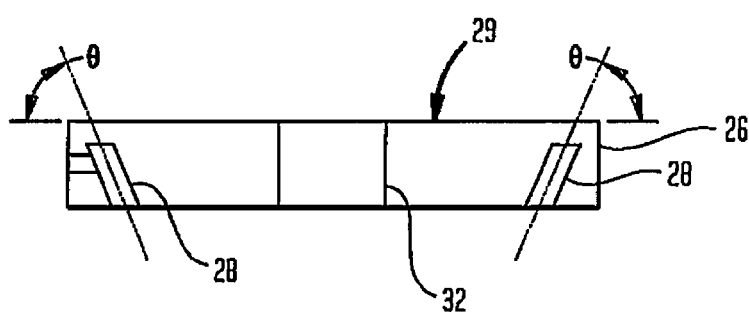

With reference to FIG. 1 and FIG. 2A, the atomizer 26 may be arranged within a center portion of a member 31 of the vessel 12. The atomizer 26 may have a generally disc shape and may have an outer dimension or diameter D which is larger than that of the rod 18. The atomizer 26 may include a through hole 32 located in the center thereof. Such hole 32 may have a size or diameter in the range of approximately 0.125 to 0.5 inches. Additionally, the atomizer 26 may include a plurality of holes 28 each located at a distance R from the center of the atomizer and near the periphery thereof. As best shown in FIG. 2B, each of the holes 28 may be inclined, that is, positioned at a predetermined angle θ with regard to an outer surface 29 of the atomizer 26. Such predetermined angle θ may have a value in the range of approximately 20 degrees to 70 degrees.

Each of the holes 28 may be coupled to a fluid supply 50 by way of a connection, such as a hose 52 or other type of connection from the fluid supply to the atomizer 26 and then by way of passages within the atomizer. The fluid supply 50 may contain a predetermined gas or liquid. As an example, such predetermined gas may be argon or nitrogen, and such predetermined liquid may be water. Additionally, the gas may be reactive with the biocompatible material. For example, the biocompatible material may be cobalt chrome and the gas may be methane or a blend having methane. The fluid may be contained within the supply 50 under a relatively high pressure, such as 60-300 pounds per square inch (psi).

The stopper rod 18 may have a generally cylindrical shape and may be configured so as to be movable within the crucible 20 along a Z direction between a first position in which the stopper rod is located on surface 29 of the atomizer 26 and a second position in which the stopper rod is located above the surface 29. More specifically, the stopper rod 18 may have a diameter which is smaller than that of hole 25 of the crucible 20 as previously indicated and larger than that of the hole 32 of the atomizer 26. As a result, when the stopper rod 18 is positioned in its first position, the stopper rod may be arranged on top of the hole 32 and may cover hole 32 so as to prevent material from passing from inside the crucible 20 to the second portion 16 of the vessel 12. And, when the stopper rod 18 is arranged in its second position, the stopper rod will not cover hole 32 so as to enable material to pass from inside the crucible 20 to the second portion 16 of the vessel 12.

A number of induction coils 22 may be arranged around the crucible 20. More specifically, such induction coils 22 may be arranged in a spiral manner around the outside and/or inside of the container 20. The induction coils 22 may be tubes fabricated from a predetermined material, such as copper, having a fluid such as water inside thereof. An electric current having a predetermined value, such as approximately 6000 amperes (amps), may be applied to the induction coils 22. Applying such current or power to the induction coils 22 may cause the material contained within the crucible 20 to be moved or stirred in a predetermined direction, such as in an up/down direction as indicated by arrows 30. Additionally, when activated, such induction coils 22 may apply heat to the crucible 20 so as to cause the materials contained therein to be heated to a predetermined temperature. As an example, such predetermined temperature may be approximately 200 to 300 degrees Centigrade over the melting point of at least one material contained in the crucible 20. As a result, and during operation, the materials contained within the crucible 20 may be stirred/mixed together and may be heated to a predetermined temperature.

Additionally, one or more heaters 36 may also be arranged on and/or in the crucible 20. Such heater or heaters 36 may be operable to apply heat to the crucible 20 to cause the materials contained therein to be heated. The heaters 36 may be utilized to supplement the heat provided by use of the induction coils 22. Alternatively, the heaters 36 may be utilized as the primary source of heat. As an example, consider the situation wherein the induction coils 22 are not used and instead another device is utilized to stir the materials in the crucible 20. In such situation, if the other device does not provide heat or does not provide sufficient heat, then the heaters 36 may be utilized.

During operation, the rod 18 may be placed in its first position so that the hole 32 in the atomizer 26 is covered. Thereafter, a desired biocompatible material (such as cobalt chrome) and a desired carbon or carbide source (such as graphite) may be added to the crucible 20. The amounts of the cobalt chrome and carbon or carbide source which are added may be dependent upon the desired amount of carbon or carbide in the final material. For example, if the resultant desired material is to be a cobalt chrome alloy having a 75 percent carbide phase or content, then one part cobalt chrome would be added for each three parts of carbide. This ratio of 1:3 may be by weight or volume. After the desired amounts of cobalt chrome and carbide are added to the crucible 20, a current (such as 6000 amps) may be applied to the induction coils 22 so as to cause the materials contained within the crucible 20 to be stirred or mixed in the up/down direction as indicated by the arrows 30, and heated to a predetermined temperature such as 200 to 300 degrees over the melting point of the one of the materials contained in the crucible 20 which has the lower melting point temperature (which, as an example, may be the cobalt chrome). Additionally, the heater(s) 36 may be activated so as to supplement the heating of the materials (cobalt chrome and carbide) in the crucible 20. At the predetermined temperature (which is the lower melting point temperature of the two melting point temperatures associated with the materials inside the crucible 20), the material in the crucible 20 which has the higher melting point temperature (which may be the carbide source) may dissolve or go into solution. Such material may then be in a solid diffusion state.

Thus, the induction coils 22 and/or the heaters 36 may be activated for a sufficient time so as to enable the materials contained within the crucible 20 to be properly mixed together and heated to the predetermined temperature. As a result, the biocompatible material or alloy (such as cobalt chrome) may be melted and the carbide source may be allowed to go into solution so as to form a molten homogeneous solution.

Thereafter, the stopper rod 18 may be moved along the Z direction from its first position to its second position so as to uncover the hole 32 in the atomizer 26. As a result, the molten homogeneous solution from the crucible 20 may pass through the hole 32 in the atomizer 26 and into the second portion 16 of the vessel 12. At the same time or prior to such time, the high pressure fluid (which may be a gas such as argon or nitrogen or which may be a liquid such as water) from the supply 50 may be supplied by way of hoses 52 to the inclined holes 28 in the atomizer 26. As a result, a high pressure gas or liquid may be supplied into the portion 16 in a direction as indicated by arrows 38 while particles 40 of the molten homogeneous solution from the crucible 20 are supplied into the portion 16 as indicated in FIG. 1. Such directed high pressure gas or liquid may impinge the particles 40 of the molten homogeneous solution so as to form spray atomized powder of a final material which, in the current example, may be a cobalt chrome alloy having a 75 percent carbide phase.

Figure 3A:
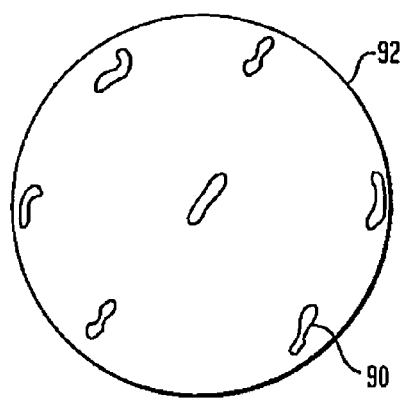
FIGS. 3A and 3B are diagrams of a top view and a side view, respectively, of an item to which reference will be made in explaining a disadvantage of a material with relatively large size carbide particles.
Figure 3B:
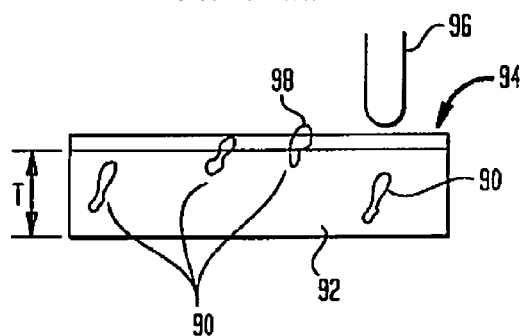
Figure 3C:
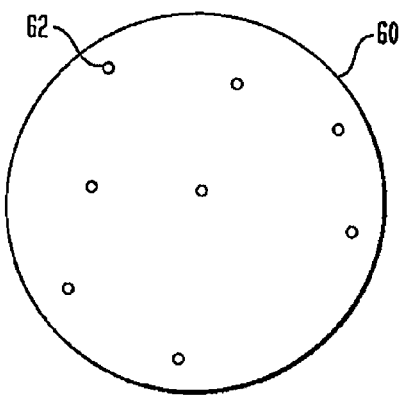
FIG. 3C is a diagram to which reference will be made in describing an item having a relatively high carbide content produced by use of the system of FIG. 1.

The final produced material (i.e., the cobalt chrome alloy having a 75 percent carbide phase) may contain carbide particles which are substantially smaller than those previously described with reference to FIGS. 3A and 3B. As an example, and with reference to FIG. 3C, the size of a carbide particle 62 contained within an item 60 formed from the final produced material may have a value less than approximately nine hundred (900) nanometers and may preferably be within the range of approximately 10-200 nanometers. As is to be appreciated, even though the carbide particles are relatively strong, since the size of the carbide particles 62 is relatively small, a machining operation of a surface of item 60 may not have the difficulties previously described with regard to an item having relatively large size carbide particles (such as that described with reference to FIGS. 3A and 3B).

Thus, the system 10 enables a biocompatible material (such as a cobalt chrome alloy) to be formed which has a carbide content or phase of 75 percent.

Although in the above example, a carbide content of 75 percent was desired, the present invention is not so limited. In fact, the system 10 may be utilized to obtain a biocompatible material with a carbide or carbon content having other values, such as, a carbide content from approximately ten (10) percent up to nearly 100 percent. As an example, the system 10 may be utilized to obtain a biocompatible material with a carbide content of 10, 15, 25, 50, 75 or even approximately 99 percent of the total weight of the formed material.

In another embodiment, a carbon or carbide source in a powder form may be added to a desired biocompatible material in a powder form and mixed together so as to form a powder mixture thereof. Particles of the powdered carbon or carbide source may have a size within a predetermined range and particles of the powdered biocompatible material may have a size within a predetermined range. By adding a desired amount of the carbon or carbide source to a given amount of the biocompatible material, the resultant powder mixture may have the desired amount of carbon or carbide. Accordingly, such procedure may produce a biocompatible material having a relatively high concentration of a carbon or carbide constituent. Further, since the size of the particles of the powdered carbon or carbide source is relatively small, the obtained mixture may contain only very small sized particles of the carbon or carbide source. As a result, items formed from the obtained mixture may be easily machined in a manner similar to that previously described with regard to FIG. 3C. As in the previously described embodiment, in this embodiment, the amount or percent of carbon or carbide in the final material may have any of a number of values. For example, the carbide content may have any value from approximately 10 percent up to nearly 100 percent (such as 15, 25, 50, 75 or even 99 percent) of the total mixture by weight. Additionally, in this embodiment, the biocompatible alloy may be one of cobalt chrome, titanium (Ti), a titanium alloy, zirconium (Zr), a zirconium alloy, stainless steel, or a cobalt based super alloy; and the carbon or carbide source may be one of graphite, coke, pitch, diamond, or diamond dust.

The above-described mixing process may be performed by a low intensity blending method. In such blending method, the biocompatible material and the carbide or carbon source may be blended together by the use of a V-blender, a shaker blender, or similar compatible type device.

Although several methods have been described herein for producing material having a relatively high carbon or carbide content, the present invention is not so limited. That is, various other methods may be utilized. As an example, powder metallurgy techniques may also be utilized to produce such material. Examples of such powder metallurgy techniques may include a mechanical alloying method in which the biocompatible material and the carbide source are blended together by using metal balls; a cryogenic milling method which is similar to the mechanical alloying method except performed under cryogenic conditions at a liquid nitrogen or liquid helium temperature; a fused and crush powder method in which the biocompatible material and the carbide source are mechanically blended, then the powder is fused by use of a furnace (wherein the powder is fused but not sintered), and then crushed to a desired size; or a powder cladding method in which a first or core material (e.g., cobalt chrome) is arranged over a second material (e.g., carbide).

In a cryogenic milling method or a mechanical alloying method, the size of the carbide particles which are started with could have a relatively large size, such as 1 millimeter or more. As a result of either method, the carbide particles may be refined so as to end up with nano-size particles. With regard to the mechanical alloying method, the size of the metal balls, the number of the metal balls, the material of the metal balls, the speed, and the volume of the container used may all affect the size of the carbide particles. Also, in a cryogenic milling method, the particles of the biocompatible metal (along with the carbide) may be refined so as to end up with nano-size particles. However, in a mechanical alloying method, the particles of the biocompatible metal may not be refined to nano-size particles.

In a low intensity mechanical blending method, the size of the carbide particles which are started with may be nano-size particles. In a fused and crush powder method, the size of the carbide particles which are started with may be nano-size particles; however, such starting particle size may be larger (such as 5-250 microns).

In a powder cladding method, nano-size carbide particles may be started with and they may be cladded with metal in a chemical vapor deposition (CVD) process. Alternatively, nano-size metal particles may be started with and they may be cladded with carbide particles which are also nano-sized (CVD process).

Accordingly, as described above, the particles of carbide used to produce a material having a relatively high carbon or carbide content may either start as nano-sized particles or after processing end up as nano-sized particles. Such size may be within the range of less than approximately 900 nanometers and may preferably be within the range of approximately 10-200 nanometers, although the size thereof may be smaller or larger. Additionally, the size of a particle of the biocompatible material in powder form may be approximately 2-300 microns. Further, during the processing, nano-size carbide particles may be clustered together with the particles of the biocompatible material to form a number of agglomerate particles each having a size in the range of approximately 2-300 microns, although such size may be larger or smaller.

Although in the above description of the above embodiments the carbon or carbide source may have been indicated to be graphite and the biocompatible material may have been indicated to be cobalt chrome or an alloy thereof, the present invention is not so limited. Instead, other materials may be used for the carbon or carbide source and for the biocompatible material.

Although the invention herein has been described with reference to particular embodiments and modifications thereof, it is to be understood that these embodiments are merely illustrative of the principles and applications of the present invention. It is therefore to be understood that numerous other modifications may be made to the illustrative embodiments and that other arrangements may be devised without departing from the spirit and scope of the present invention as defined by the appended claims.

The invention claimed is:

1. Method of fabricating a material having a high concentration of a carbide constituent and utilizing said material to coat at least one surface of a component, said method comprising:
   adding a carbide source to cobalt chrome or an alloy thereof, in which a weight of the carbide source is at least approximately 50% of a total weight of the carbide source and the cobalt chrome or the alloy thereof and in which the carbide source includes graphite;
   heating the carbide source and the cobalt chrome or the alloy thereof to a predetermined temperature to melt the cobalt chrome or the alloy thereof and allow the carbide source to go into solution so as to form a molten homogeneous solution; and
   impinging the molten homogeneous solution with a high pressure fluid so as to form spray atomized powder having carbide particles, in which a size of a carbide particle in the atomized powder is approximately 900 nanometers or less, and
   coating the at least one surface of the component with the spray atomized powder having carbide particles.

2. The method according to claim 1, in which the size of said carbide particle in the atomized powder is within a range of approximately 10-200 nanometers.

3. The method according to claim 1, in which the predetermined temperature is approximately 200-300 degrees Centigrade over a melting temperature of the cobalt chrome or the alloy thereof.

4. The method according to claim 1, in which the fluid is a gas.

5. The method according to claim 4, in which the gas is argon or nitrogen.

6. The method according to claim 1, in which the fluid is a liquid.

7. The method according to claim 6, in which the liquid is water.

8. The method according to claim 1, in which the weight of the carbide source is at least approximately 75% of the total weight of the carbide source and the cobalt chrome or the alloy thereof.

9. The method according to claim 1, in which the weight of the carbide source is at least approximately 99% of the total weight of the carbide source and the cobalt chrome or the alloy thereof.

* * * * *